United States Patent [19]

Shah et al.

[11] Patent Number: 5,322,695

[45] Date of Patent: Jun. 21, 1994

[54] MOISTURE-VAPOR-PERMEABLE DRESSING

[75] Inventors: Kishore R. Shah, Bridgewater; Agis Kydonieus, Kendall Park; Dimitrios Apostolopoulos, Highland Park, all of N.J.

[73] Assignee: Hercon Laboratories Corporation, New York, N.Y.

[21] Appl. No.: 932,747

[22] Filed: Aug. 25, 1992

Related U.S. Application Data

[63] Continuation of Ser. No. 771,858, Oct. 19, 1991, abandoned, which is a continuation of Ser. No. 2,024, Jan. 9, 1987, abandoned.

[51] Int. Cl.$^5$ .................... A61L 15/00; A61F 13/00
[52] U.S. Cl. ................... 424/448; 604/304; 604/307; 424/445; 424/446; 424/447; 424/449; 602/54; 602/58
[58] Field of Search ............. 604/304, 306, 307; 424/424, 445, 446, 447, 448, 449; 128/155

[56] References Cited

U.S. PATENT DOCUMENTS

| Re. 31,886 | 5/1985 | Hodgson | 428/40 |
|---|---|---|---|
| Re. 31,887 | 5/1985 | Hodgson | 428/355 |
| 3,598,122 | 8/1971 | Zaffaroni | 128/268 |
| 3,645,335 | 2/1972 | Hodgson | 161/146 |
| 3,710,795 | 1/1973 | Higuchi et al. | 128/260 |
| 3,734,097 | 5/1973 | Zaffaroni | 128/268 |
| 3,921,636 | 11/1975 | Zaffaroni | 128/260 |
| 4,310,509 | 1/1982 | Berglund et al. | 424/28 |
| 4,379,454 | 4/1983 | Campbell et al. | 604/897 |
| 4,542,012 | 9/1985 | Dell | 424/28 |
| 4,576,818 | 3/1986 | Shetty | 424/150 |
| 4,596,738 | 6/1986 | Metcalfe et al. | 428/308.4 |
| 4,657,006 | 4/1987 | Rawlings | 604/307 |
| 4,706,662 | 11/1987 | Thompson | 128/156 |

FOREIGN PATENT DOCUMENTS

| 930668 | 7/1973 | Canada . |
| 0174803 | 3/1986 | European Pat. Off. . |
| 0177329 | 4/1986 | European Pat. Off. . |
| 0184465 | 6/1986 | European Pat. Off. . |
| 0184910 | 6/1986 | European Pat. Off. . |
| 3520011 | 6/1984 | Fed. Rep. of Germany . |
| 2143564 | 2/1973 | France . |
| 8600536 | 1/1986 | PCT Int'l Appl. . |
| 1361289 | 7/1974 | United Kingdom . |
| 2160420 | 1/1986 | United Kingdom . |

OTHER PUBLICATIONS

Business Week, Oct. 5, 1981 "A Bandage That Acts Like Skin", p. 381.

*Primary Examiner*—Marianne M. Cintins
*Assistant Examiner*—Catherine Scalzo
*Attorney, Agent, or Firm*—Sughrue, Mion, Zinn, Macpeak & Seas

[57] ABSTRACT

Described is a moisture-vapor-permeable and oxygen-permeable adhesive dressing for use in supplying a topical medicament to human skin in a controlled release manner, which dressing is unaffected by and impermeable to water in the liquid phase, which dressing when in use on human skin consists essentially of:

(i) a polymeric backing material lamina having two surfaces, a first substantially planar surface and a second substantially planar surface;

(ii) adhering to said first planar surface of said backing material a medication reservoir lamina having two surfaces, a first substantially planar surface and a second substantially planar surface, consisting essentially of an intimate mixture of:
  (a) a polyvinyl chloride polymer;
  (b) a polymeric plasticizer intimately admixed with said polyvinyl chloride and compatible with said polyvinyl chloride; and
  (c) a topical medicament compatible with said polyvinyl chloride and said plasticizer;

said first substantially planar surface of said medication reservoir lamina adhering to said first substantially planar surface of said backing material in a continuous or discontinuous manner; and (iii) adhering to said second substantially planar surface of said medication reservoir lamina, a pressure-sensitive adhesive which is permeable to oxygen and moisture vapor but is unaffected by liquid water.

11 Claims, 5 Drawing Sheets

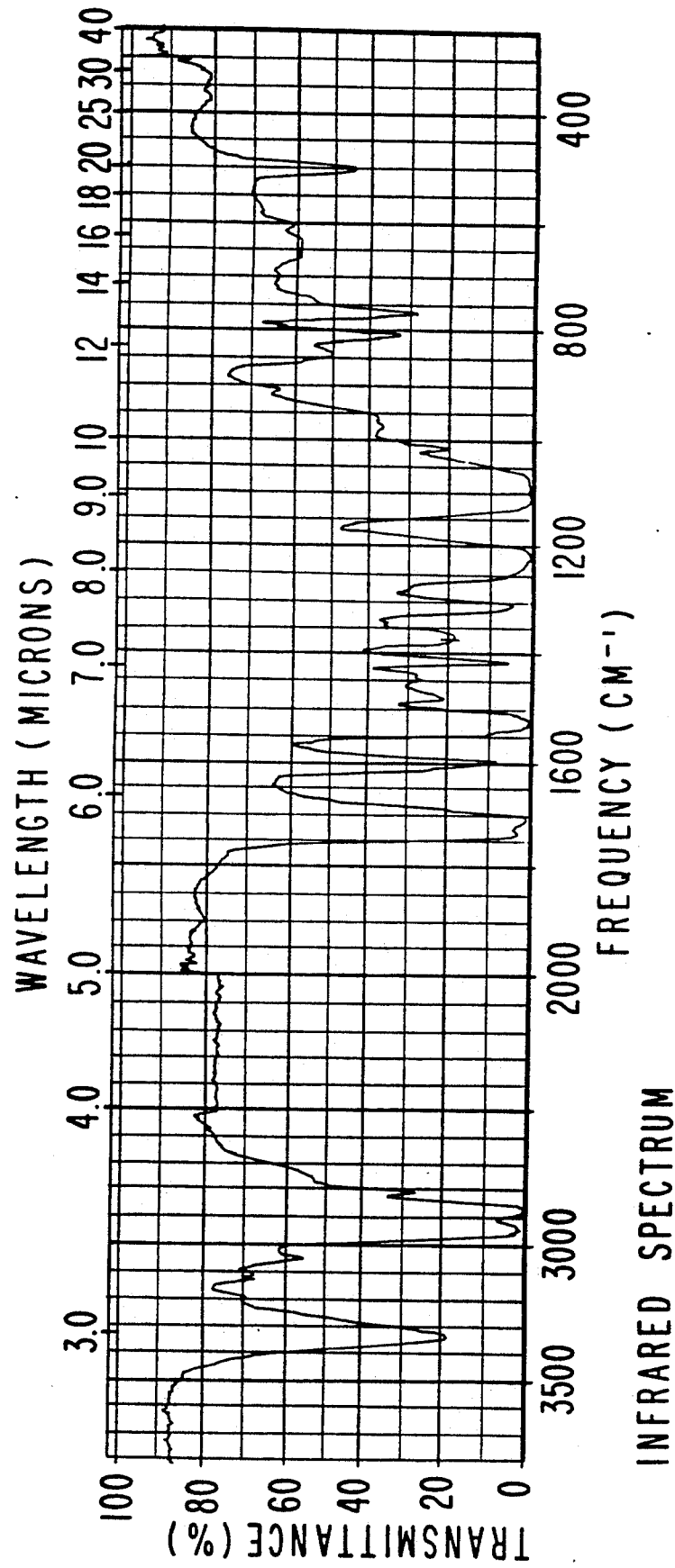
FIG.6 INFRARED SPECTRUM

MOISTURE-VAPOR-PERMEABLE DRESSING

This is a continuation of application Ser. No. 07/771,858 filed Oct. 8, 1991, now abandoned, which is a continuation of application Ser. No. 07/002,024 filed Jan. 9, 1987, now abandoned.

BACKGROUND OF THE INVENTION

1. Field of the Invention

This invention relates broadly to articles of manufacture for administration of topical medicaments to human skin (as opposed to systemically active drugs) in a controlled release manner. The articles are moisture-vapor-permeable and oxygen-permeable but are impermeable to water in the liquid phase. The articles consist essentially of:

(i) a polymeric backing which in many instances is elastomeric*;

*The terms "elastomeric" and "elastomer" are herein intended to cover polymers having reasonable degrees of elasticity; however, such "elastomer polymers" are to be expected to have finite yields. Thus, for example, an "elastomer" is a polymer herein intended to have an elongation greater than 150% under applied stress.

(ii) adhering to one surface of the polymeric backing, a medication reservoir which is a mixture of a polyvinyl chloride polymer, a polymeric plasticizer and a topical medicament. Adhering to the medication reservoir on a surface opposite to backing layer is a pressure sensitive adhesive. Examples of topical medicaments useful in the practice of our invention are tolnaftate, chlorhexidine, chlorhexidine esters, chlorhexidine salts, hydrocortisone, benzalkonium salts, benzethonium salts and polyvinyl pyrrolidone-iodine complexes.

2. The Prior Art

A relatively new concept in wound management is the use of thin transparent elastomeric film dressings as opposed to conventional gauze dressings. Such elastomeric film dressings are known in the prior art and consist usually of a polyurethane film with a laminated pressure-sensitive adhesive for adhesion to the skin. The elastomeric film dressings of the prior art have high moisture vapor and oxygen permeability which properties are believed to be responsible for faster wound healing (of the order of 40% faster than when using conventional gauze dressings). The polyurethane film dressings of the prior art act as barriers to bacteria and liquid water, thus minimizing the risk of infection. Subsequent to 1980, the concept of the elastomeric film dressing has gained acceptance in hospital practice at a progressively rapid rate. The single most use of the polyurethane elastomeric film dressing is as a device for securement of peripheral and central intravenous catheters. Other applications are as a wound dressing for decubitus ulcers, autograft donor sites and partial thickness skin loss wounds. Existing commercial products of the prior art include OP-SITE ® produced by T. J. Smith and Nephew Limited of Kingston-Upon-Hull, England, TEGADERM ® produced by the Minnesota Mining and Manufacturing Company of St. Paul, Minn., BIOCLUSIVE ® manufactured by the Johnson & Johnson Company of New Brunswick, N.J., POLYSKIN ® manufactured by the Kendall Company, Division of Colgate Palmolive Company and ENSURE-IT ® manufactured by the Deseret Medical Company, Division of Becton Dickinson of Franklin Lakes, N.J.

In the article "A Bandage That Acts Like Skin" in BUSINESS WEEK of Oct. 5, 1981, at page 381, it is disclosed that hospital studies indicate that OP-SITE ®, a transparent polyurethane film cuts healing time by up to 40% compared with the usual gauze bandage.

U.S. Pat. No. 3,645,835 issued on Feb. 29, 1972 and reissued as Re. U.S. Pat. Nos. 31,886 on May 14, 1985 and 31,887 on May 14, 1985 (assigned to T. J. Smith & Nephew Limited) discloses a moisture-vapor-permeable pressure-sensitive adhesive material for use on animal skin comprising a backing material and a pressure-sensitive adhesive on at least substantially the whole of the body adhering portion of at least one surface of the backing material, both the backing material and the adhesive being moisture-vapor-permeable and unaffected by water; with at least one of the backing material and/or the adhesive comprising a synthetic polymer and being continuous and non-permeable to liquid water, the adhesive material have a moisture-vapor-permeability of at least 300 grams/square meter/24 hours/40° C./80% relative humidity. It is indicated therein that a preferred backing material is a polyurethane film.

U.S. Pat. No. 4,596,738 issued on Jun. 24, 1986 assigned to Smith and Nephew Associated Companies p.l.c. discloses a moisture vapor transmitting elastomeric film which comprises a blend of incompatible polymers and contains voids characterized in that the blend comprises a continuous matrix of ethylene vinyl acetate within which the incompatible polymer forms a discrete particulate phase matrix and further discloses that the film is liquid water impermeable and has a moisture-vapor transmission rate of at least 500 g/m$^2$/24 hours at 37° C. at 100% to 20% relative humidity difference.

European Patent Application 174 803 filed on Sep. 5, 1985 assigned to Smith and Nephew Associated Companies p.l.c. discloses a bacteria proof adhesive wound dressing having a moisture vapor transmission rate of greater than 300 g/m$^2$/24 hours at 37° C. at 100% to 10% relative humidity difference and which comprises a film which is coated on one face by an adhesive layer and has bonded to its other face a layer of foam. It is further disclosed therein that the foam is preferably a reticulated polyurethane foam from 0.5 to 2 mm thick.

U.S. Pat. No. 4,310,509 issued on Jan. 12, 1982 assigned to Minnesota Mining and Manufacturing Company of St. Paul, Minn. discloses a pressure-sensitive adhesive having homogeneously dispersed therein a broad-spectrum antimicrobial agent. It is further disclosed that when the composition is placed in contact with the skin, it uniformly and controllably releases the broad-spectrum antimicrobial agent with substantially unaltered broad-spectrum antimicrobial activity. Exemplified is the polyvinyl pyrrolidone iodine complex. Similarly, U.S. Pat. No. 4,323,557 discloses the polyvinyl pyrrolidone-iodine complex in the pressure-sensitive adhesive.

U.S. Pat. No. 4,542,012 issued on Sep. 17, 1985 discloses a dermatologically acceptable film-forming composition comprising a film-forming polymer and as a broad spectrum antimicrobial agent, iodine which forms a complex with the film-forming polymer. It is further disclosed therein that the compositions when applied to skin from a fugitive solvent form a substantially water-insoluble tack-free flexible film which adheres to the skin, releases the antimicrobial agent when the film is in contact with the skin and exhibits an elongation of at least about 150%.

German Offenlegungsschrift 3520 011 and United Kingdom Application 2,160,420 assigned to Yissum Research and Development Company disclose a composition for topical application for the gradual release of iodine comprising a hydrophilic polyurethane as a carrier of the iodine. It is further disclosed that the compositions release iodine in a gradual and predetermined manner over a prolonged time. It is further disclosed therein that the physical properties of the carrier and the germicidal properties of the iodine result in the prevention or control of infections, in exudate absorption, in crust removal and in rapid healing of sores because of the iodine release when the composition is applied to sores, wounds, burns and skin damage.

PCT Patent Application 86/00536 assigned to Avery International Corporation discloses a bandage for the transdermal or topical administration of a drug over an extended period of time comprising an impermeable backing sheet, a solid drug pellet on the backing sheet and a layer of contact adhesive covering the pellet and backing sheet. Control over the rate of dissolution of the solid drug can be achieved by varying the type of web fabric, the type of adhesive and the thickness of the adhesive.

U.S. Patent No. 4,576,818 issued on Mar. 18, 1986 provides iodophors which exhibit effective degerming of skin, mucous membranes of animals and surfaces of inanimate objects which provide broad spectrum microbicidal action. The iodophors of 4,576,818 are complexes of iodine with polydextrose or with the polymer resulting from the copolymerization of sucrose and epichlorohydrin.

European Patent Application 184 465 filed on Dec. 6, 1985, assigned to Warner-Lambert Company discloses an antithrombogenic thermoplastic polyurethane product comprising a substrate and at least one layer of a polyurethane alloy complex comprising a thermoplastic polyurethane and completely dispersed therein a preformed complex of an antithrombogenic material and/or an antibiotic agent ionically bonded with a quaternary ammonium compound.

U.S. Pat. No. 3,598,122 assigned to the Alza Corporation and issued on Aug. 10, 1971 discloses a bandage for use in the continuous administration of systemically active drug by absorption through the skin comprising a backing member having on one surface thereof a reservoir containing a systemically active drug. The reservoir has a wall distant from the backing member and permeable to the passage of the drug. The pressure-sensitive adhesive layer also permeable to the passage of the drug is carried by the reservoir.

U.S. Pat. No. 3,734,097 issued on May 22, 1973 discloses an adhesive laminate tape for the topical administration of a controlled therapeutically effective quantity of drug which may be selected from the group consisting of antineoplastic agents, folic acid antagonists and antimitotic agents for the treatment of skin lesions comprising a backing member bearing a pressure-sensitive adhesive, the adhesive having distributed therein a means for metering the flow of a therapeutically effective amount of the drug to the lesions over a prolonged period of time.

European Published Application 177 329 filed on Oct. 1, 1985 discloses a device for transdermal administration of nitroglycerin comprising a solid vinyl plastisol layer for contacting the patient's skin, the layer containing from about 40-70% of an emulsion polymerized polyvinyl chloride resin, from about 25-45% plasticizer and from about 5-20% nitroglycerin, and a backing layer opposite the skin-contacting surface as a barrier to the release of nitroglycerin.

Canadian Patent 930,668 discloses a bandage for administering drugs comprised of a backing member, a pressure sensitive adhesive, and at least one reservoir disposed between the backing member and pressure sensitive adhesive. The reservoir is comprised of a systemically active drug formulation confined within a wall member, the wall member being formed from a drug release rate controlling material. The reservoir can be in the form of discrete microcapsules or distinct reservoir compartments or layers. The reservoir can also be in the form of walled containers having one or more interior drug-containing chambers, as well as solid matrixes having a systemically active drug distributed therethrough. The Canadian patent discloses a wide variety of materials which can be used to form the reservoir. Among the materials mentioned are silicone rubbers, hydrophilic polymers of monoesters of an olefinic acid, polyvinylalcohol, polyvinylacetate, plasticized polyvinylchloride, plasticized nylon, collagen, modified collagen, getain and waxes such as polyethylene wax, oxidized polyethylene wax, hydrogenated castor oil and the like, with the silicone rubbers being preferred. The Canadian patent does not contain any examples showing the use of plasticized polyvinyl chloride, and does not show the use of a PVC plastisol.

Similarly, Zaffaroni, U.S. Pat. No. 3,921,636 issued on Nov. 25, 1975 discloses a drug delivery device for administering a drug at a controlled rate for a prolonged period of time comprising a plurality of reservoirs containing drug distributed through a matrix. The reservoirs and the matrix are formed of materials permeable to passage of the drug. The rate of drug permeation from the reservoir is lower than the rate of permeation through the matrix so that release from the reservoir is the drug release rate controlling step. Thus, Example 6, at column 15, lines 5-30 of U.S. Pat. No. 3,921,636 relates to a polyvinyl chloride resin containing plasticizer and prednisolone disodium phosphate thusly:

A drug delivery device for the controlled, oral administration of water-soluble prednisolone is prepared as follows: first, a plurality of drug reservoirs comprising porous, discrete particles of polymerized poly(vinyl chloride) of about 100 microns diameter are prepared by mixing 100 g of suspension grade poly(vinyl chloride) resin with 50 g of octyl diphenyl phosphate and 10 g of prednisolone disodium phosphate at room temperature into a sticky, wet mass. Next, the temperature of the mixture is raised to 80° C. for about 3 to 7 minutes, while stirring, to form dry, free flowing, discrete drug reservoirs. The reservoirs are uniformly dispersed through a matrix by mixing 50 g of reservoirs containing the prednisolone with 140 g of polydimethylsiloxane, 10 g of silicone oil, and 0.5 g of stannous octoate. After mixing the ingredients, the mixture is charged into pill molds and allowed to cure for 30 minutes. Oral administration of the resulting device yields a controlled essentially constant rate of release of prednisolone phosphate to the gastrointenstinal tract to give a more uniform blood level of prenisolone over a longer period of time than is achieved when prednisolone alcohol is administered by standard prior art pills.

Furthermore, as is well known, polyvinyl chloride (PVC) is never used alone, but is always mixed with other ingredients before being processed. Polyvinyl chloride appeared initially to be an unpromising resin because of its thermal instability and high rigidity. PVC, however, was then discovered to form a rubber-like material when dissolved hot in high boiling solvents known as plasticizers and cooled to room temperature. PVC is now available in a number of different physical forms and types, and its manufacture depends on the form desired. Thus, PVC is available as a vinyl latex, a dispersion resin, or a general purpose resin. PVC latexes are true colloidal dispersions of submicrometer particles in water, stabilized by a surfactant system, and need plasticizers in order to form a continuous film. The PVC in vinyl latex is manufactured by emulsion polymerization.

Dispersion resins are produced by emulsion polymerization and are mixed with plasticizers to form a colloidal dispersion. Such dispersions are known as plastisols and are easily handled and readily pourable. When heated to a temperature of about 148° to 177° C., the plastisol is transformed to a homogeneous melt which, upon cooling to below 50° C., results in a tough flexible product. The PVC resins made by emulsion polymerization are hard spheres of particle size between about 0.05 and 20 microns, such as between 1 and 20 microns. They do not have the ability to absorb plasticizers. Therefore, a mixture containing, for example, 30% plasticizer and 70 PVC resin, produces a flowable liquid, known as plastisol.

General purpose PVC resins are made by mass and suspension polymerization process, and comprise the largest amount of PVC resins produced, such as at least 80% of all PVC resins, and are used chiefly to make so-called 100% vinyl products by a variety of molding and extrusion techniques. Resins intended for flexible applications should have good uptake of plasticizer in a dry blending operation and contain more than 25% of a plasticizer system. PVC compounds that contain less than 25% plasticizers are referred to as semirigid compounds. The PVC resins manufactured by suspension and bulk polymerization are 50 to 200, such as 100 to 150 microns in diameter, and are like sponges. They are capable of absorbing large amounts of plasticizers, so that even a 50% plasticizer, 50% PVC resin composition would result in a non-flowing, solid material.

SUMMARY OF THE INVENTION

It is an object of the present invention to provide an article of manufacture which offers enhanced delivery capability of a topical medicament to human skin in a controlled release manner directly from a plasticized vinyl resin layer (preferably a "plastisol") in which the topical medicament is incorporated in required high concentrations.

This invention also enables the administration of topical medicaments such as tolnaftate, chlorhexidine, chlorhexidine esters, chlorhexidine salts, hydrocortisone, benzalkonium salts, benzethonium salts and iodine to be achieved through an article of manufacture, e.g., a controlled release delivery device requiring contact over the entire affected area of a patient tissue.

Thus, this invention is directed to a moisture-vapor-permeable and oxygen-permeable adhesive dressing for use in supplying a topical medicament to human skin in a controlled release manner which dressing is unaffected by and impermeable to water in the liquid phase, which dressing when in use on human skin consists essentially of:

(i) a polymeric (and in many instances "elastomeric") backing material lamina;

(ii) adhering to one side of the polymeric backing material lamina, a medication reservoir lamina which is a mixture of a polyvinyl chloride resin containing a polymeric plasticizer and a topical medicament compatible with the polyvinyl chloride resin and adhering to the other side of the plasticized polyvinyl chloride resin layer a pressure-sensitive adhesive unaffected by liquid water.

BRIEF DESCRIPTION OF THE DRAWINGS

FIG. 6 is the infrared spectrum of the polyester-polyurethane polymer used as the backing material in Examples II-XII, infra and indicated by reference numerals 17 in FIGS. 1 and 25 in FIG. 2, supra.

DETAILED DESCRIPTION OF THE INVENTION

The invention is described herein with respect to preferred embodiments including topical medicament delivery devices containing various topical medicaments including but not limited to:

(i) benzethonium chloride having the structure:

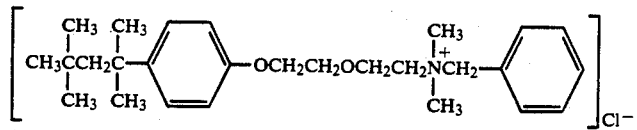

(benzyldimethyl(2-(2-(p-1,1,3,3-tetramethylbutylphenoxy)ethoxy)-ethylammonium chloride);

(ii) benzalkonium chloride having the structure:

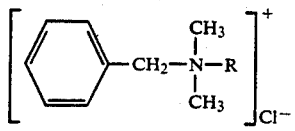

wherein R represents $C_8H_{17}$ up to $C_{18}H_{37}$ alkyl (defined according to U.S. Pat. 2,157,047);

(iii) hydrocortisone having the structure:

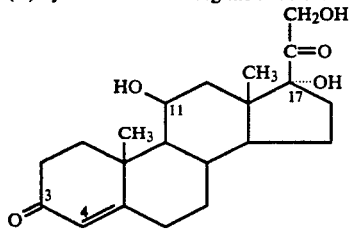

(4-pregnene-11 beta, 17 alpha, 21-triol-3,20-dione);

(iv) tolnaftate having the structure:

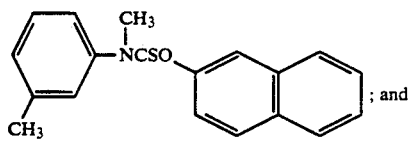
; and (v) chlorhexidine diacetate hydrate having the structure:

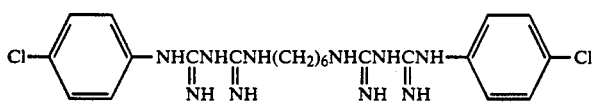

It will be understood that other embodiments may be employed within the spirit and scope of this invention. Thus, the foregoing examples are also intended to include the genuses, to wit:
(i) chlorhexidine, per se;
(ii) chlorhexidine esters;
(iii) chlorhexidene salts;
(iv) benzalkonium salts; and
(v) benzethonium salts.

In addition, another example of a topical medicament is iodine delivered through the substance polyvinylpyrrolidone-iodine complex.

Thus, the articles of our invention are useful for the application of a topical medicament to human skin in a controlled release manner. The articles of our invention are moisture-vapor-permeable and oxygen-permeable and are essentially impermeable to water in the liquid phase. The articles of our invention consist essentially of:
(i) a polymeric backing material (in many instances, an "elastomeric" backing material) lamina having two surfaces, a first substantially planar surface and a second substantially planar surface;
(ii) adhering to said first planar surface of said backing material, a medication reservoir lamina having two surfaces, a first substantially planar surface and a second substantially planar surface consisting essentially of an intimate admixture of:
 (a) a polyvinyl chloride polymer;
 (b) a polymeric plasticizer intimately admixed with said polyvinyl chloride and compatible with said polyvinyl chloride; and
 (c) a topical medicament compatible with said polyvinyl chloride and said plasticizer;
said first substantially planar surface of said medication reservoir lamina adhering to said first substantially planar surface of said backing material in a continuous or discontinuous manner and adhering to said second substantially planar surface of said medication reservoir lamina a pressure-sensitive adhesive which is permeable to oxygen and moisture vapor but is unaffected by liquid water.

Figure 1:
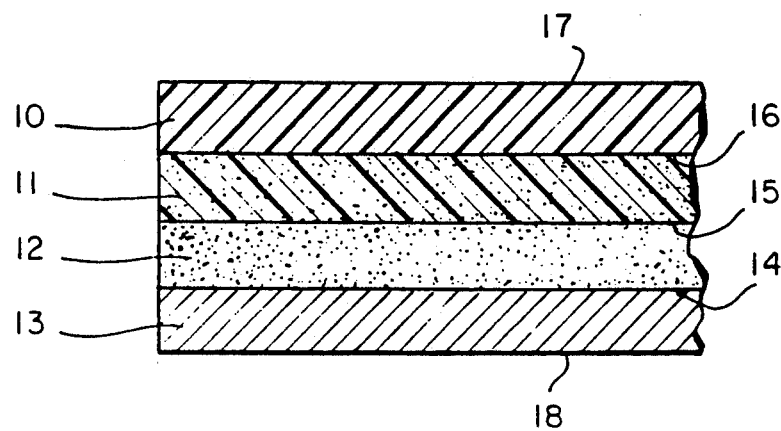
FIG. 1 is a cross-sectional view of a preferred topical medicament delivery device in accordance with this invention.
Figure 2:
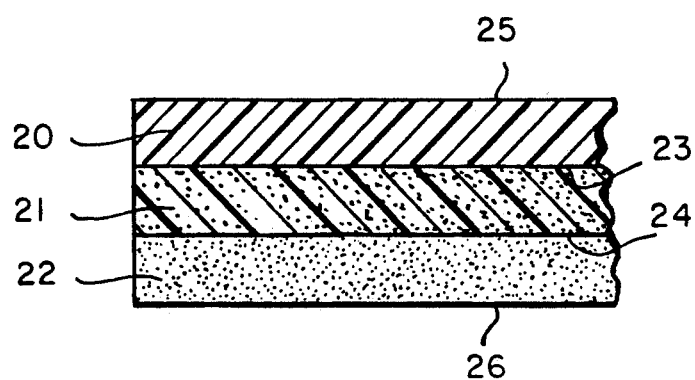
FIG. 2 is another cross-sectional view of a second preferred topical medicament delivery device in accordance with this invention.

In FIG. 1 and in FIG. 2 a cross-section of two embodiments of the article of our invention are set forth. In FIG. 1, the backing layer is indicated by reference numeral 10. The topical medicament reservoir is indicated by reference numeral 11. The pressure-sensitive adhesive is indicated by reference numeral 12. Optionally, prior to use, a peelable layer 13 is removably adhered to the adhesive layer 12. The outer surface of the backing layer is indicated by reference numeral 17. The surface of the backing layer adhered to the reservoir layer is indicated by reference numeral 16. The surface of the reservoir layer adhered to the pressure-sensitive adhesive layer is indicated by reference numeral 15. The surface of the pressure-sensitive adhesive layer adhered to the peelable backing layer is indicated by reference numeral 14. The surface of the peelable backing layer away from the adhesive layer is indicated by reference numeral 18.

Referring to FIG. 2, the backing material lamina is indicated by reference numeral 20 with an outer surface 25 and an inner surface 23 to which is continuously adhered a medication reservoir lamina 21 having an outer surface 24 to which is adhered a pressure-sensitive material 22 having an outer surface 26.

The polymeric backing material lamina indicated by reference numeral 10 in FIG. 1 and reference numeral 20 in FIG. 2 has a thickness of between 0.5 and 1.5 mils (between 0.0005 and 0.0015 inches) and is composed preferably of a mixture of polyurethane and polyvinyl chloride; from about 5 up to about 20% by weight of polyvinyl chloride and from about 95 down to 80% by weight of polyurethane. Such films possess the required combination of breathability (oxygen and moisture vapor permeability) and handling and wear characteristics.

The over-all range of thickness of the article of our invention including backing layer, medication reservoir, and pressure-sensitive adhesive may vary from about 2.0 mils up to about 6.0 mils with a preferable maximum thickness of 4 mils.

Tests concerning the oxygen and water vapor permeability of the films, particularly the backing layer, of our invention are set forth infra.

The medication reservoir is comprised of a plasticized polyvinyl chloride resin (polyvinyl chloride in admixture with a non-migratory polymeric plasticizer), preferably, a "plastisol", containing the required concentration of the desired topical medication. Examples of topical medication used in the polyvinyl chloride resin are as follows:
(i) benzethonium chloride;
(ii) benzalkonium chloride;
(iii) hydrocortisone;
(iv) tolnaftate;
(v) chlorhexidine; and
(vi) polyvinylpyrrolidone-iodine complex.

When using tolnaftate, the percent of tolnaftate in the polyvinyl chloride resin may vary from about 0.5% up to about 3.0%. When using chlorhexidine diacetate hydrate, for example, from about 2 up to 12% by weight of the chlorhexidine diacetate hydrate may be used based upon the total weight of the medication reservoir. When using hydrocortisone, from about 0.25% up to about 3.0% by weight of the hydrocortisone based on the total weight of medication reservoir may be used. When using benzalkonium chloride, from about 0.1% up to about 1.0% by weight of the benzalkonium chloride may be used based upon the total weight of the medication reservoir. When using benzethonium chloride, from about 0.1% up to 1% by weight of the benzethonium chloride based upon the total weight of the medication reservoir may be used. Preferred concentrations of topical medicament in the medication reservoir are set forth in the examples provided infra.

Thus, when using polyvinylpyrrolidone-iodine complex, between about 7% and about 11% by weight of the weight of medication reservoir may be used.

As stated supra, the moisture-vapor-permeable and oxygen-permeable dressing for use in supplying a topical medicament to human skin in a controlled release manner is to be impermeable to water in a liquid phase. Accordingly, the article of our invention must have a moisture-vapor-permeability of at least about 25 g/square meters/24 hours at 25° C. and at 75% relative humidity; preferably, at least about 40 g/square meter/24 hours at 25° C. and at 75% relative humidity. Accordingly, the polymeric backing material lamina of our invention can be a material other than the preferred polyurethane-polyvinyl chloride backing and can, in fact, be any of the backing materials set forth at column 5 and column 6 of Reissue Pat. No. 31,886 issued on May 14, 1985, the specification for which is incorporated by reference herein. These include copolymers produced by copolymerizing in an inert atmosphere an alkoxy alkyl acrylate or methacrylate with a different alkoxy acrylate or methacrylate.

The medication reservoir as stated supra consists essentially of polyvinyl chloride and a polymeric plasticizer. The plasticized PVC layer contains from about 20 up to about 70% by weight of a polyvinyl chloride resin which consists essentially of a vinyl chloride polymer containing, predominantly or completely repeating vinyl chloride monomeric units and in an amount of less than about 10% other repeating vinyl units, e.g., repeating vinyl acetate units; from about 20% up to about 70% by weight of the composition of one or more polymeric plasticizers; and from about 0.25% up to about 15% by weight of the total composition of a topical medicament, such as tolnaftate, chlorhexidine, chlorhexidine esters, chlorhexidine salts, hydrocortisone, benzalkonium salts, benzethonium salts or a polyvinylpyrrolidone-iodine complex or mixtures of the foregoing as exemplified hereinafter.

Figure 4:
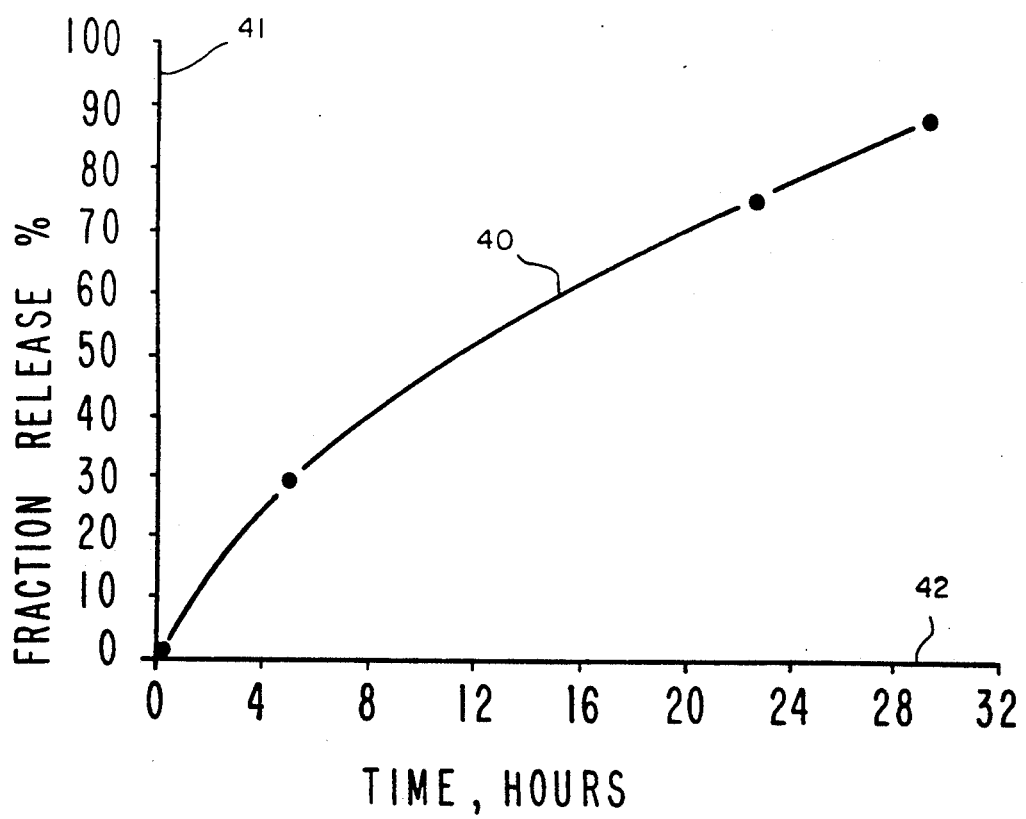
FIG. 4 is a graph showing the fraction of release (weight percentage) versus time in hours for the release of hydrocortisone from a dressing as illustrated in FIG. 2.

It has now been found that the release rate of active topical medicaments which is uniformly dispersed in the plasticized PVC layer is dependent upon the proportion of PVC resin the composition. Thus, for example, the release follows the curve for hydrocortisone according to FIG. 4.

The reservoir layers of this invention are relatively weak insofar as their tensile strengths are concerned and usually less than about 1500 psi (highly flexible and soft materials). In contrast, the flexible vinyl films of commerce are considerably stronger materials exhibiting tensile strengths of the order of from about 1500 up to about 5000 psi. The polyvinyl chloride resin content of the commercially useful and available flexible vinyl films ranges from 50 to 75%. Such materials do not have adequate topical medicament permeating characteristics to serve as suitable topical medicament delivery reservoirs. For example, a film for delivery of tolnaftate contains 43% polyvinyl chloride, 1% tolnaftate and 56% ADMEX ®, a polymeric plasticizer. A film containing chlorhexidine diacetate hydrate contains 41% polyvinyl chloride, 4% chlorhexidine diacetate hydrate and 55% ADMEX ®. The film containing hydrocortisone contains 42.5% polyvinyl chloride, 0.5% hydrocortisone and 57% ADMEX ®. The film containing benzalkonium chloride contains 48.8% polyvinyl chloride, 0.2% benzalkonium chloride and 51% ADMEX ® as is the case with the film containing benzethonium chloride. This will be apparent from a reading of the examples set forth infra.

The topical medicament supplying devices of our invention comprise a plasticized polyvinyl chloride resin layer and a a topical medicament agent substantially uniformly dispersed in the PVC layer which may be referred to as a reservoir for the topical medicament. The polyvinyl chloride reservoir in the present invention is prepared from a polyvinyl chloride resin and a primary polymeric plasticizer for the resin.

Preferably, the polyvinyl chloride resin employed in the preferable practice of the present invention is that which is specifically used in preparing PVC plastisols, namely PVC resins which are made by the well known emulsion polymerization process, which are hard spheres of particle size between 0.05 and 20 microns, such as between 1 and 20 microns, between 1 and 5 microns or between 0.05 and 1 microns, and which do not have the ability to absorb plasticizers to any great extent. Instead, the plasticizer wets the resin particles at room temperature and only then very slowly penetrates and solvates the resin. These PVC resins when mixed with the polymeric plasticizers such as a mixture of 30% polymeric plasticizer and 70% PVC resin, give a flowable liquid known as a "plastisol" which can then be fused at, for example, approximately 300° F. for approximately 60 seconds to provide a solid polymer layer. The PVC resin employed in the present invention is in contrast to the general purpose PVC resins which are produced by suspension or bulk polymerization and which are used in calendering and extrusion processes, which are 50 to 200 microns, such as 100 to 150 microns in diameter, and are like sponges. Thus, the general purpose resins are capable of absorbing large amounts of plasticizers so that even a 50% ADMEX ® and 50% PVC resin would result in a non-flowing solid material. The molecular weight of the PVC resins employed in the present invention preferably is a weight average molecular weight between 80,000 and 250,000, such as a weight average molecular weight of 123,000. A suitable polyvinyl chloride resin is one sold by Occidental Chemical Company under the designation FPC 6338 containing about 96% vinyl chloride monomer units and about 4% vinyl acetate monomer units. Thus, the polyvinyl chloride resin can be a copolymer containing preferably at least 90% by weight vinyl chloride monomer units, such as a copolymer based on vinyl chloride and vinyl acetate.

The polyvinyl chloride resin generally is present in the layer in an amount of from about 10 up to 50% weight percent, preferably 20 to 50 weight percent based on the total weight of the plasticized PVC composition.

The primary polymeric plasticizer which is employed in the present invention can be polymeric adipate plasticizers, which are polymers of adipic acid with a monomer, such as propylene glycol and, for example, can be obtained under the designation Drapex 334F from Witco Chemical Corporation, or any otherknown polymeric plasticizer for PVC which is biologically acceptable.

Thus, other examples of polyester adipates, glutarates and sebacates are:
polyester adipate P-644;
polyester glutarate P-530;
polyester glutarate P-540;
polyester glutarate P-550;
polyester glutarate P-7035;
polyester glutarate P-7035M;
polyester glutarate P-7046;
polyester glutarate P-7092; and
polyester sebacate P-1070
manufactured by the C. P. Hall Company, 7300 S. Central Avenue, Chicago, Ill. 60638. Other preferred polymeric plasticizers are those which are known as "adipate" plasticizers, for example, ADMEX ® 760 which is a high molecular weight linear adipate plasticizer manufactured by the Sherex Division of Nuodex Inc. In general, polyester plasticizers which are polyesters of (i) adipic acid, 1,4-terephthalic acid and/or 1,2-phthalic acid with (ii) polyethylene glycols, ethylene glycol or 1,3-propylene glycol having molecular weights in the range of 4000–10,000 are preferred.

The polymeric plasticizer generally is present in an amount of between about 50 and 70% based on the total weight of plasticized PVC layer.

With reference to FIGS. 1 and 2, the blended plasticized PVC containing, for example, PVC, ADMEX ® and hydrocortisone is then coated at a rate of about 36 ounces/yd² on a backing and then fused into solid plasticized PVC layer 11. The backing as stated supra is a single layer of drug impermeable polymer composition, preferably the polyvinyl chloride-polyurethane mixture as set forth supra.

The thickness of the medication reservoir lamina 11 (in FIG. 1) and 21 (in FIG. 2) is preferably about 1 mil but may vary from about 0.5 mils up to about 1.5 mils (from about 0.0005 inches up to about 0.0015 inches) with the total thickness of the article of our invention including the backing layer, the medication reservoir lamina and the self adhesive layer being preferably about 3 mils.

Backing 10 in FIG. 1 and backing 20 in FIG. 2 substantially blocks loss of topical medicament from the plasticized PVC layer 11 in FIG. 1 and 21 in FIG. 2 other than in the direction of the surface which contacts self adhesive layer 12 in FIG. 1 and 22 in FIG. 2.

The self adhesive layer 12 in FIG. 1 and 22 in FIG. 2 is permeable to the topical medicament and may be continuous or discontinuous. After peeling away the peelable layer 13 from surface 14 in FIG. 1, the article of FIG. 1 may be adhered to that part of the skin which is to be subjected to treatment using the topical medicament located in lamina 11. The topical medicament in lamina 11 then is transported across junction 15 through the self adhesive layer 12 in FIG. 1 or is transported from medication reservoir 21 across junction 24 through self adhesive layer 22 across surface 26 onto the skin.

The blended plasticized PVC which is coated onto the backing 10 in FIG. 1 and backing 20 in FIG. 2 can be fused into a homogeneous solid by heating it for a short period, such as 30 to 60 seconds at a temperature of, for example, 250° to 300° F. The use of a plasticized PVC to form solid layer 11 in FIG. 1 and solid layer 21 in FIG. 2 enables layers 11 and 21 to be formed using a low temperature for a short period of time and provides conditions which do not affect the stability of the topical medicament.

When not in use, the entire surface intended for skin contact, e.g., surface 14 in FIG. 1 and surface 24 in FIG. 2 is preferably covered with a release layer, e.g., a release paper, such as release paper 13 in FIG. 1 which is removed to expose the surface of adhesive layer 14 and topical medicament containing plasticized PVC layer 11 for application to the patient's skin.

The self adhesive layer 12 in FIG. 1 and 22 in FIG. 2 may be continuous or discontinuous as stated supra. In any case, the self adhesive may be any compatible self adhesive which will permit diffusion of the topical medicament therethrough (if, indeed, it is continuous) such as those set forth with specificity in Re. U.S. Pat. No. 31,886 issued on May 14, 1985, the specification for which is incorporated herein by reference. The example of a useful adhesive is that set forth in Example 3 at columns 12 and 13 of said Re. U.S. Pat. No. 31,886. Other self adhesives are set forth in U.S. Pat. No. 3,734,097 issued on May 22, 1973, the specification for which is incorporated by reference herein.

The thickness of the self adhesive layer may vary from about 0.5 mils up to about 2 mils with a preferred thickness of self adhesive layer being about 1 mil.

The invention will now be described with reference to the following examples. In these examples where reference is made to moisture-vapor permeabilities, the units are grams/square meter/24 hours at 25° C. at 75% relative humidity.

EXAMPLE I

Oxygen and Water Vapor Permeation of the Medicated Wound Dressing Film Containing a Polyvinyl Pyrrolidone-Iodine Complex The permeation of a gas or water vapor through a polymer film can be described in terms of the gas or water vapor dissolving at one surface of the film, diffusing through the film under a concentration gradient and evaporating from the other surface at the low concentration side.

If a constant pressure difference is maintained across the film, the gas vapor will diffuse through the film at a constant rate. Under steady state conditions the permeability process is described by equation 1.

$$J = \frac{DS(p_1 - p_2)}{L} \quad \text{(Eq. 1)}$$

where:
J = the amount of gas or water vapor diffusing through unit area of the film in unit time at standard temperature and pressure.
D = the diffusion coefficient.
S = the solubility coefficient.
$p_1 - p_2$ = the pressure difference maintained across the film.
L = the film thickness
The product D.S is defined a Permeability Constant (P) and is calculated from the equation 2.

$$P = DS = \frac{JL}{p_1 - p_2} \quad \text{(Eq. 2)}$$

The permeability constant is expressed terms of quantities given below.

$$P = \frac{(\text{amount of gas or water vapor}) \times (\text{thickness})}{(\text{Area}) \times (\text{Time}) \times (\text{Pressure Difference})}$$

Materials and Methods

The material tested for oxygen and water vapor premeation were the following:
1. A 1 mil thick Polyurethane film of a lower modulus, supplied by General Foam Corp.
2. A 1 mil thick film of Polyurethane blended with 10% of PVC, supplied by Norwood Industries, Inc..
3. A 3 mil thick PVC film of flesh color.
4. A 4.5 mil thick medicated wound dressing Film (illustrated in FIG. 1) containing an iodine complex and a surfactant (IGEPAL ® CO-630) in a dissolved form.
5. A 5 mil thick medicated wound dressing Film (illustrated in FIG. 1) containing an iodine complex and a surfactant (IGEPAL ® CO-630) in a dissolved form.
6. A 5 mil thick medicated wound dressing Film (illustrated in FIG. 1) containing an iodine complex in a dispersed form.
7. A 2 mil thick medicated wound dressing film manufactured by Minnesota Mining and Manufacturing Company of St. Paul, Minn. (TEGADERM ®).

The structure and composition characteristics of the wound dressing films #4, #5 and #6 are presented in FIGS. 1 and 2 and Table 1 respectively.

The oxygen and water vapor permeabilities of the plain and wound dressing films were determined using the concentration increase method. The method employed a permeation cell which after being mounted with 5 cm² of film sample consisted of two different compartments. While the lower compartment was filled with nitrogen, the upper compartment was flushed continuously with oxygen humidified at a level of 65–75% (temperature = 25° C.). The oxygen humidification was accomplished by passing an oxygen gas steam through a washing bottle filled with deionized water. The oxygen and water vapor from the upper compartment diffused through the tested film into lower compartment and changed its composition with time. The oxygen and water vapor concentration changes in the lower cell compartment were determined by chromatography. A research chromatograph (Hewlett Packard-5750) was used for the chromatographic analysis. This chromatograph was equipped with a thermal conductivity detector and two 6'×¼" O.D. aluminum columns. Column #1 was packed with CTR1 and Column #2 with PORAPAK ® Q. The CTR1 column was used for oxygen and the PORAPAK ® Q column for water vapor analysis. The GC operational conditions were as follows:

| | Oxygen Analysis | Water Vapor Analysis |
|---|---|---|
| Column temperature: | 25° C. | 150° C. |
| Detector temperature: | 150° C. | 250° C. |
| Injection port temperature: | 150° C. | 250° C. |
| Carrier gas: | Helium | Helium |
| Carrier gas flow rate: | 120 cc/min | 50 cc min |
| Filament current: | 150 ma | 157 ma |

RESULTS AND DISCUSSION

The oxygen and water vapor permeability constants determined for the various wound dressing and other films are presented in Table 2. As it can be seen from this table, the oxygen permeability of the wound dressing films is not as high as that of the control. However, it can be considered sufficient enough to ensure permeation of the needed oxygen for wound healing. The high water vapor permeability constants of the same wound dressing films indicates that sweat or moisture can easily permeate through, which otherwise would collect on the inside surface of the film causing discomfort and possible adhesive failure.

TABLE 1

| Composition of Medicated Wound Dressing Films |
|---|
| 1. Medicated wound dressing film containing an iodine complex in a dissolved form. |

| Plasticizer: | 55% (ADMEX ®) |
|---|---|
| PVC Resin: | 21% |
| PVP-Iodine Complex: | 8.6% |
| Ethanol: | 15.4% |

2. Medicated wound dressing film containing an iodine complex and a surfactant (IGEPAL ® CO-630) in a dissolved form.

| Plasticizer: | 55% (ADMEX ®) |
|---|---|
| PVC Resin: | 21% |
| PVP-Iodine Complex: | 8% |
| Surfactant: (IGEPAL ® CO-630): | 1% |
| Ethanol: | 15% |

3. Medicated Wound Dressing Film Containing an iodine complex in a dispersed form.

| Plasticizer: | 65% (ADMEX ®) |
|---|---|
| PVC Resin: | 25% |
| PVP-Iodine Complex: | 10% |

The curing conditions for the above wound dressing films were as follows:

| Temperature: | 300° F |
|---|---|
| Curing Time: | 1 minute |

TABLE 2

Oxygen and Water Vapor Permeability Constants of Medicated Wound Dressing and Other Films

| Material | $O_2$ Permeability Constant at 25° C. and 65% Relative Humidity (Per Unit Thickness) $\frac{(cm^3 O_2 \text{ mil})}{(m^2 \text{ day atm.})}$ | $O_2$ Permeability For Product of 3 Mils $\frac{(cm^3 O_2)}{(m^2 \text{ day atm.})}$ | Water Vapor Permeability Constant at 25° C. and 75% Relative Humidity (Per Unit Thickness) $\frac{(g\ H_2O\ \text{mil})}{(m^2 \text{ day atm.})}$ | Water Vapor Permeability For Product of 3 Mils $\frac{(g\ H_2O)}{m^2 \text{ day atm.}}$ |
|---|---|---|---|---|
| Polyurethane Film | 4451 | — | 123.40 | — |
| Film of Polyurethane with 10% polyvinyl chloride | 2710 | — | 113.63 | — |
| Polyvinyl chloride film | 2226 | — | 22.04 | — |
| Wound Dressing Film with polyvinyl-pyrrolidone-iodine complex dissolved | 6421.50 | 2140.50 | 379.10 | 126.30 |
| Wound Dressing with Polyvinylpyrrolidone-iodine complex and IGEPAL ® CO -630 dissolved | 7725 | 2575 | 217.96 | 72.65 |
| Wound Dressing Film with Polyvinylpyrrolidone-iodine complex dispersed | 7876.5 | 2625.5 | 151.80 | 50.60 |
| Wound Dressing Film Manufactured by Minnesota Mining and Manufacturing Company of St. Paul, Minn. (TEGADERM ®) | 7208.8 | 3604.4 (For Product of 2 mils) | 147.0 | 73.50 (For Product of 2 mils) |

NOTE:
The polyurethane used is a polyurethane polyester manufactured by Semex Medical Company, subsidary of Seton Company of Malverne, Pennsylvania. It is identified according to the infrared spectrum of FIG. 6.

EXAMPLE II

Mechanical Properties of Some Polymer Films

The following polymer films were tested for their ultimate tensile strength, elongation at break and Young's Modulus and the results are as follows:

TABLE 3

Mechanical Properties of Some Polymer Films

| Sample | Thickness (Mils) | Initial Length (In) | Width (In) | Strain Rate (In/Min) | Peak Load (PDS) | Ultimate Tensile (PDS/In²) | Break Extension (In) | Elongation (%) | Young's Modulus (Kg/cm²) |
|---|---|---|---|---|---|---|---|---|---|
| Polyvinylchloride Film | 3 | 8 | 1 | 12 | 4.78 | 3187 | 7.03 | 87.84 | 8514 ± 464 |
| Polyurethane Film with a Lower Modulus | 1 | 3 | 0.5 | 12 | 2.98 | 5960 | 13.75 | 458.3 | 1480 ± 56 |
| Polyurethane Film Containing 5% Polyvinylchloride | 1 | 8 | 0.5 | 12 | 1.58 | 3153 | 21.72 | 271.5 | .3158 ± 0 |
| Polyurethane Film Containing 10% Polyvinylchloride (First Sample) | 1 | 8 | 0.5 | 12 | 1.67 | 3340 | 14.36 | 179.50 | 8070 ± 604 |
| Polyurethane Film Containing 10% Polyvinylchloride (Second Sample) | 1 | 8 | 1 | 12 | 3.10 | 3101 | 15.28 | 190.96 | 11236 |

Figure 3:
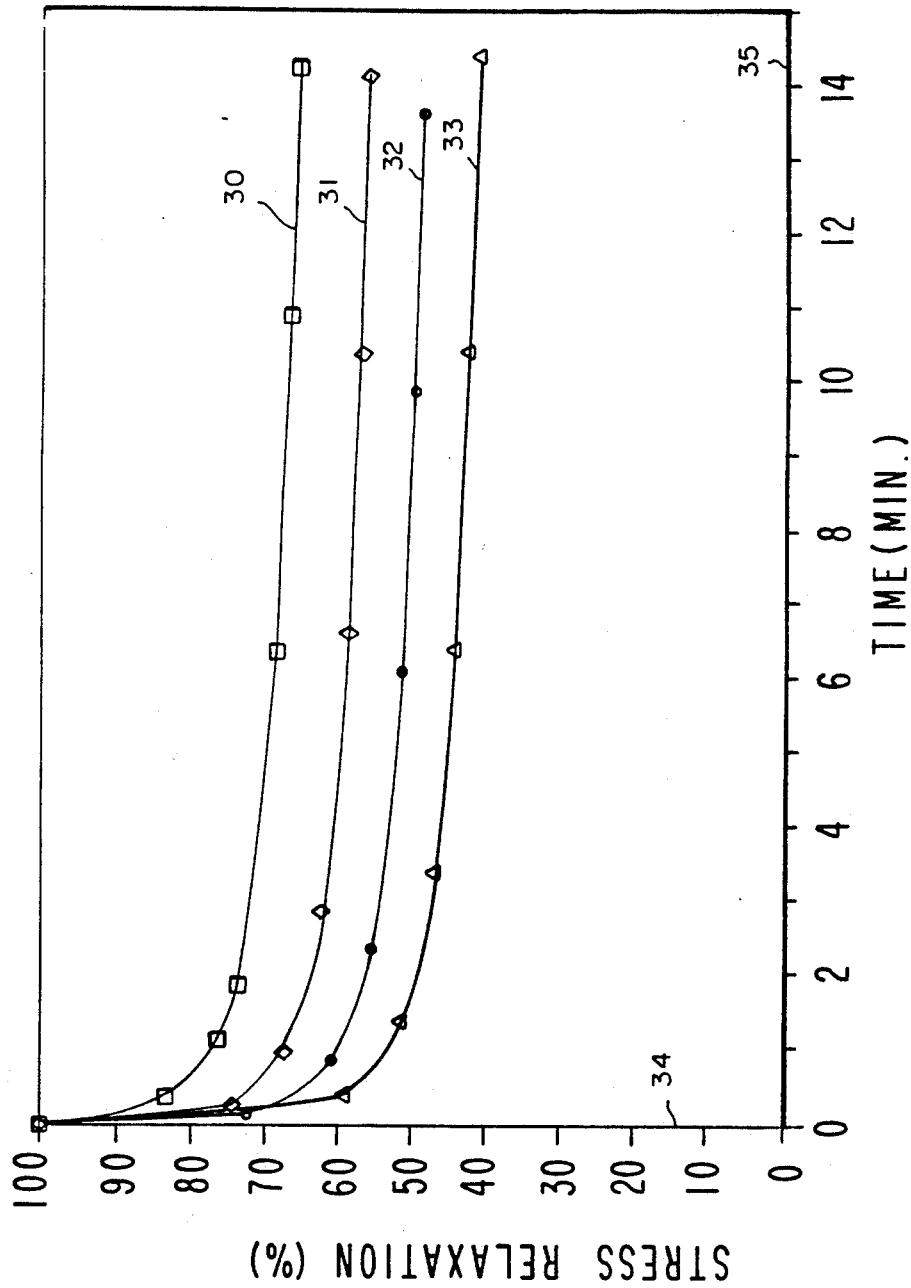
FIG. 3 is a graph of stress relaxation versus time for various polyvinyl chloride, polyurethane and polyurethanepolyvinyl chloride backing films.

FIG. 3 sets forth a graph of stress relaxation of various materials versus time. The graph indicated by reference numeral 30 is the graph for polyurethane film which is the polyester polyurethane identified according to the infrared spectrum of FIG. 6. The graph indicated by reference numeral 31 is the graph for the polyurethane resin also containing 5% polyvinyl chloride. The graph indicated by reference numeral 32 is a graph for the polyurethane resin containing 10% by weight of polyvinyl chloride. The graph indicated by reference numeral 33 is a graph for polyvinyl chloride per se (time versus stress relaxation) (percent).

EXAMPLE III

Antibacterial Activity Evaluation of the Wound Dressing Film Containing Polyvinylpyrrolidone-Iodine Complex

Objective

The objective of this study was to find out if the wound dressing film could release sufficient amount of iodine necessary to maintain the microenvironment of a wound free of bacteria.

Materials and Methods

The medicated wound dressing films submitted for antibacterial activity determination were the following:
1. A wound dressing film containing 11.2% of polyvinylpyrrolidone-iodine complex;
2. A wound dressing film containing 24% of polyvinylpyrrolidone-iodine complex;
A porous pressure sensitive adhesive, supplied by Norwood Industries, Inc., was used as face adhesive on both films (#1 and #2).
3. A wound dressing film containing 24% of iodine complex. The adhesive used with this sample was the #408 supplied by the Minnesota Mining and Manufacturing Company.
4. Control—the IOBAN ® 2-6635 antimicrobial film of Minnesota Mining and Manufacturing Company of St. Paul, Minn.

The composition and structure characteristics of the wound dressing films are presented in Table 4 and FIGS. 1 and 2.

The antibacterial activity of the tested samples was determined by using the AATCC Method 90. Staphylococcus aureus and Escherichia coli cultures were used to evaluate the product's efficiency on human skin, and its activity in preventing the spread of enteric disease. The incubation period was 24 hours at 37° C.

Results and Discussion

The results of the antibacterial activity evaluation obtained for the tested wound films are presented in Table 5. As can be seen from this table 5, the wound dressing films of our invention performed as well as the control. There was no zone of inhibition surrounding the samples. Bacterial growth did not occur, only where there was direct contact between the wound dressing films and the culture medium.

TABLE 4

| Composition of the Wound Dressing Films Submitted for Antibacterial Activity Determination | |
|---|---|
| Wound Dressing Film #1 | |
| Polyvinylpyrrolidone-iodine complex: | 11.2% |
| ADMEX ® Plasticizer: | 49.6% |
| PVC Resin (6338): | 37.8% |
| Polyvinylpyrrolidone: | 1.4% |
| Wound Dressing Films #2 and #3 | |
| Polyvinylpyrrolidone-iodine complex: | 24% |
| ADMEX ® Plasticizer: | 42% |
| Polyvinyl chloride resin (6338) | 29.5% |
| Polyvinylpyrrolidone (molecular weight 40,000): | 4.5% |

TABLE 5

| Results of the Antibacterial Activity Evaluation | | |
|---|---|---|
| Sample Identification | Staphylococcus Aureus | Escherichia Coli |
| Sample with 11.2% of polyvinylpyrrolidone-iodine complex and a porous face adhesive | No growth | No growth |
| Sample with 24% of polyvinylpyrrolidone-iodine complex and a porous face adhesive | No growth | No growth |
| Sample with 24% of polyvinylpyrrolidone-iodine complex and Minnesota Mining and Manufacturing Company #408 face adhesive | No growth | No growth |
| Control (IOBAN ® 2) | No growth | No growth |

EXAMPLE IV

Hydrocortisone Film Dressing

A. In Vitro Hydrocortisone Release Testing

The release of hydrocortisone from the film dressing of our invention was studied using Franz diffusion cells employing 20% aqueous propylene glycol as the receptor phase. Samples of the receptor phase were taken at different time intervals and analyzed for hydrocortisone using ultraviolet spectroscopy. The release profile (FIG. 4 (indicated by reference numeral 40 with the axis for time in hours indicated by reference numeral 42 and the axis for fraction release indicated by reference numeral 41)) indicated that 25% and 75% of the total hydrocortisone in the sample was released within periods of 4 hours and 24 hours, respectively.

The in vitro data illustrates the sustained hydrocortisone release capability of the film dressing of our invention. In in vivo performance on skin, the sustained release of hydrocortisone would be expected to maintain its saturation concentration at the skin surface.

B. Product Indications and Advantages

For antiinflammatory action in the treatment of pruritic, allergic and atopic dermatitis. As compared to an ointment, the film dressing is more convenient to use, because it is non-greasy and is not wiped off by clothes or washed away by water. Permits greater freedom of movement to the patient.

Longer lasting action.

Breathability and skin-like appearance and wear can enhance patient acceptance.

Experimental

A. Materials

Acetone and isopropyl alcohol, supplied by VWR Scientific Propylene glycol, supplied by Fisher Scientific Hydrocortisone, supplied by Sigma Chemical Company Plasticizer (ADMEX ® 760), supplied by Nuodex, Inc. PVC resin 6338, supplied by Occidental Co.

Gelva 737 adhesive, supplied by Monsanto.

Film of polyurethane blended with 10% PVC, supplied by Norwood Industries, Inc.

Aerosil 200 (silica powder) supplied by Degussa Inc.

B. Methods

Dissolution Study

This study was designed to determine the release of hydrocortisone from the dispenser of FIG. 1 as affected by the amount of active drug (hydrocortisone), plasticizer (ADMEX ®) and PVC resin in the reservoir. In addition, the effect of various face adhesives on the transport and release of hydrocortisone was evaluated.

Construction of the Hydrocortisone Dispenser

All formulation ingredients were dissolved in a solvent (isopropyl Alcohol/Acetone: 2/1) and mixed thoroughly to get a suspension. Furthermore, this suspension was cast on a release liner, using a Gardner knife, to get the reservoir preferably 1 mil thick. The reservoir was stripped of the residual solvent by placing it for 30 minutes in an oven set at 90° C. The PVC-polyurethane backing film was then laminated to one side of the reservoir by simultaneously passing both of them through a hot nip laminator. The operating conditions for the laminator were as follows:

| Temperature: | 300° F. |
|---|---|
| Pressure: | 40 PSI |
| RPM: | 7 |

The construction of the hydrocortisone dispenser was completed by transferring a pressure sensitive adhesive on the other side of the reservoir after the release liner was removed.

Receiver Solution Preparation

The receiver solution used in this study was deionized water containing 20% of propylene glycol.

Cell Preparation

The Franz type diffusion cells, 0.732 cm$^2$, were used for this study. The receiver compartments were filled with 5 ml of receiver solution and one small magnetic stir bar was added to each cell. Donor reservoirs were 3/16" disks which had been punched out of a hydrocortisone dispenser. The disks were mounted on the cell and covered with aluminum foil to assure proper disk position. The top of the cell was clamped in place and the entire cell was put in a heated block (33°-34° C.). Three replicates were run.

Sampling Procedure

Samples of the receiver solution were taken at designated time intervals. The entire receiver was sample and replaced by 5 ml of fresh solution. The samples were analyzed immediately thereafter.

Sampling Analysis

Samples were analyzed for hydrocortisone, using a Perkin Elmer UV spectrophotometer set at a wave length of 247 nm. A calibration curve was used to convert absorbance values to concentration.

The cumulative hydrocortisone concentrations were then plotted as a function of time. The slopes of the lines were calculated using a regression analysis and averaged. The slop represents the release rate of hydrocortisone, (micrograms/cm$^2$-hr.).

EXAMPLES V-IX, INCLUSIVE

Figure 5:
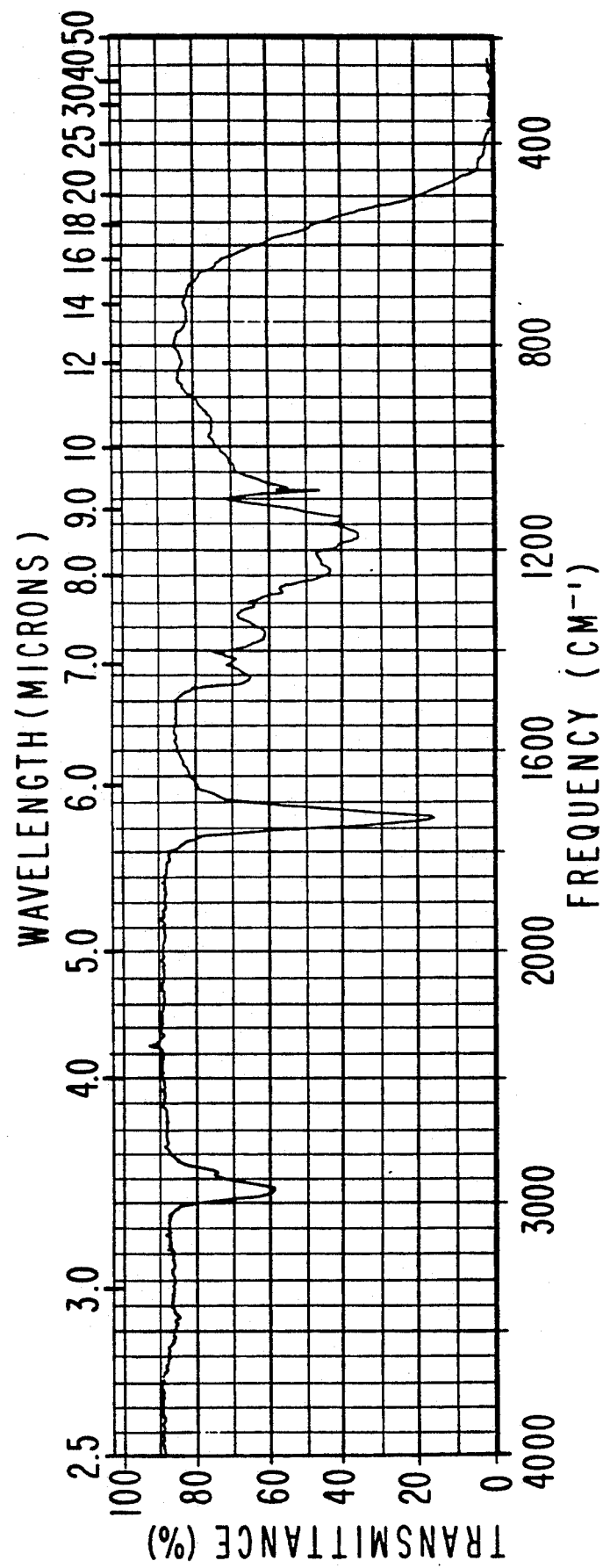
FIG. 5 is the infrared spectrum of ADMEX ® 760 as used in Examples II-XII.

In the following Examples V-IX, various topical medicaments were added in the percents indicated to the polyvinyl chloride plastisol layer and amount of drug released was measured against time. In each case, the backing film was 1 mil thick; the adhesive layer was 1 mil thick and was composed of acrylic pressure sensitive adhesive. The backing layer was 10% polyvinyl chloride and 90% polyurethane-polyester which polyurethane-polyesters defined according to the infrared spectrum of FIG. 6 and was manufactured by the Semex Medical Subsidiary of Seton Company of Malverne, Pa. In each case, the plasticizer used is ADMEX ® defined according to the infrared spectrum of FIG. 5.

Example V

Tolnaftate Film Dressing

A film dressing according to FIG. 1 was prepared wherein in the medicament reservoir layer, the following composition was prepared:

| ADMEX ® plasticizer | 56% |
|---|---|
| Polyvinyl chloride | 43% |
| Tolnaftate | 1% |

The percent of drug released over a period of time was as follows:

| Time | Percent Drug Released |
|---|---|
| 5 hours | 20% |
| 10 hours | 30% |
| 24 hours | 45% |
| 48 hours | 78% |

Example VI

Chlorhexidine Diacetate Hydrate Film Dressing

A film dressing according to FIG. 1 was prepared wherein the medicament polyvinyl chloride plastisol reservoir lamina was composed of the following composition:

| Polyvinyl chloride | 41% |
|---|---|
| ADMEX ® plasticizer | 55% |
| Chlorhexidine diacetate hydrate | 4% |

The time versus percent drug release data is as follows:

| Time | Percent Drug Released |
|---|---|
| 7 hour | 6.5% |
| 24 hours | 10.4% |
| 48 hours | 13% |

In vitro antimicrobial activity testing for this product showed a 1-2 mm wide zone of inhibition against *Staphylococcus aureus* and *Escherichia coli* bacteria.

Example VII

Hydrocortisone Film Dressing

A hydrocortisone film dressing was prepared according to the structure of FIG. 1 wherein the polyvinyl chloride plastisol medicament reservoir lamina contained the following ingredients:

| Polyvinyl chloride | 42.5% |
| --- | --- |
| ADMEX ® plasticizer | 57% |
| Hydrocortisone | 0.5% |

The percent drug released versus time is as follows:

| Time | Percent Drug Released |
| --- | --- |
| 4 hours | 20% |
| 8 hours | 34% |
| 24 hours | 70% |

Example VIII

Benzalkonium Chloride Film Dressing

A film dressing according to the construction of FIG. 1 was prepared wherein the polyvinyl chloride plastisol medicament reservoir lamina consisted of the following ingredients:

| Polyvinyl chloride | 48.8% |
| --- | --- |
| ADMEX ® plasticizer | 51% |
| Benzalkonium chloride | 0.2% |

Example IX

Benzethonium Chloride Film Dressing

A film dressing according to the construction of FIG. 1 was prepared wherein the polyvinyl chloride plastisol medicament reservoir lamina consisted of the following ingredients:

| Polyvinyl chloride | 48.8% |
| --- | --- |
| ADMEX ® plasticizer | 51% |
| Benzethonium chloride | 0.2% |

What is claimed is:

1. A moisture-vapor-permeable and oxygen-permeable adhesive dressing for use on human skin which dressing is unaffected by and impermeable to water in the liquid phase, which dressing consists essentially of:
   (i) thermoplastic-polyurethane polyvinyl chloride backing material lamina having two surfaces, a first substantially planar surface and a second substantially planar surface;
   (ii) adhering to said first planar surface of said backing material, a medication reservoir lamina having two surfaces, a first substantially planar surface and a second substantially planar surface, consisting essentially of an intimate mixture of:
      (a) a polyvinyl chloride polymer;
      (b) a polymeric plasticizer intimately admixed with said polyvinyl chloride and compatible with said polyvinyl chloride; and
      (c) a topical medicament compatible with said polyvinyl chloride and said plasticizer;
   said first substantially planar surface of said medication reservoir lamina adhering to said first substantially planar surface of said backing material in a continuous or discontinuous manner; and
      (iii) adhering to said second substantially planar surface of said medication reservoir lamina a pressure-sensitive adhesive which is permeable to oxygen and moisture vapor but is unaffected by liquid water.

2. The dressing of claim 1 wherein the moisture-vapor-permeability thereof is at least about 25 g/sq. meter/24 hours at 25° C. at 75% relative humidity.

3. The moisture-vapor-permeable and oxygen-permeable adhesive dressing of claim 1 wherein the pressure-sensitive adhesive (iii) comprises an acrylic ester copolymer containing hydrophilic groups wherein the hydrophilic group is hydroxyl, carboxyl, amine, amide, ether or alkoxy, said adhesive dressing having a moisture-vapor permeability of at least about 40 g/sq. meter/24 hours at 25° C. at 75% relative humidity, said adhesive dressing adhering continuously to said medication reservoir lamina.

4. The moisture-vapor-permeable and oxygen-permeable adhesive dressing of claim 1, wherein the polymeric backing material lamina has a thickness of between 0.5 and 1.5 mils.

5. The moisture-vapor-permeable and oxygen-permeable adhesive dressing of claim 1, wherein the dressing has an overall thickness of from about 2.0 mils up to about 6.0 mils.

6. The moisture-vapor-permeable and oxygen-permeable adhesive dressing of claim 5, wherein the overall thickness is at most 4 mils.

7. The dressing of claim 1 wherein the topical medicament is selected from the group consisting of:
   (i) tolnaftate;
   (ii) chlorhexidine;
   (III) chlorhexidine esters;
   (iv) chlorhexidine salts;
   (v) hydrocortisone;
   (vi) benzalkonium salts;
   (vii) benzethonium salts; and
   (viii) polyvinylpyrrolidone-iodine complexes.

8. A moisture-vapor-permeable and oxygen-permeable adhesive dressing for use on human skin which dressing is unaffected by and impermeable to water in the liquid phase, which dressing consists essentially of:
   (i) a thermoplastic polyurethane-polyvinyl chloride backing material lamina having two surfaces, a first substantially planar surface and a second substantially planar surface, being made from a first intimate mixture which includes polyurethane resin and polyvinyl chloride, the weight percent of polyvinyl chloride in said first intimate mixture being from about 5% up to about 20% calculated as wet weight;
   (ii) adhering to said first planar surface of said backing material a medication reservoir lamina having two surfaces, a first substantially planar surface and a second substantially planar surface, consisting essentially of a second intimate mixture of:
      (a) a polyvinyl chloride polymer;
      (b) a polymeric plasticizer intimately admixed with said polyvinyl chloride and compatible with said polyvinyl chloride; and
      (c) a topical medicament compatible with said polyvinyl chloride and said plasticizer;
   said first substantially planar surface of said medication reservoir lamina adhering to said first substantially planar surface of said backing material in a continuous manner; and (iii) adhering to said second substantially planar surface of said medication reservoir lamina a pressure-sensitive adhesive which is permeable to oxygen and moisture vapor but is unaffected by liquid water.

9. The dressing of claim 8 wherein the moisture-vapor-permeability thereof is at least about 40 g/sq. meter/24 hours at 25° C. at 75% relative humidity.

10. The moisture-vapor-permeable and oxygen-permeable adhesive dressing of claim 8 wherein the pressure-sensitive adhesive (iii) comprises an acrylic ester copolymer containing hydrophilic groups wherein the hydrophilic group is hydroxyl, carboxyl, amine, amide, ether or alkoxy, said adhesive dressing having a moisture-vapor permeability of at least about 40 g/sq. meter/24 hours at 25° C. at 75% relative humidity.

11. The dressing of claim 8 wherein the topical medicament is selected from the group consisting of:
(i) tolnaftate;
(ii) chlorhexidine;
(iii) chlorhexidine esters;
(iv) chlorhexidine salts;
(v) hydrocortisone;
(vi) benzalkonium salts;
(vii) benzethonium salts; and
(viii) polyvinylpyrrolidone-iodine complexes.

* * * * *